(12) United States Patent
Chen et al.

(10) Patent No.: US 8,722,886 B1
(45) Date of Patent: May 13, 2014

(54) METHODS FOR THE TOTAL CHEMICAL SYNTHESIS OF ENANTIOMERICALLY-PURE 7-(2'-TRIMETHYLSILYL)ETHYL CAMPTOTHECIN

(71) Applicants: Xinghai Chen, San Antonio, TX (US); Frederick H. Hausheer, Fair Oaks Ranch, TX (US); Andrey Malakhov, San Antonio, TX (US); Harry Kochat, San Antonio, TX (US)

(72) Inventors: Xinghai Chen, San Antonio, TX (US); Frederick H. Hausheer, Fair Oaks Ranch, TX (US); Andrey Malakhov, San Antonio, TX (US); Harry Kochat, San Antonio, TX (US)

(73) Assignee: BioNumerik Pharmaceuticals, Inc., San Antonio, TX (US)

( * ) Notice: Subject to any disclaimer, the term of this patent is extended or adjusted under 35 U.S.C. 154(b) by 0 days.

(21) Appl. No.: 13/694,255

(22) Filed: Nov. 13, 2012

(51) Int. Cl.
*C07F 7/02* (2006.01)
*C07D 491/147* (2006.01)

(52) U.S. Cl.
USPC .............................................. 546/14; 546/92

(58) Field of Classification Search
USPC ...................................................... 546/14, 92
See application file for complete search history.

(56) References Cited

U.S. PATENT DOCUMENTS 7,030,243 B1 * 4/2006 Wu et al. .......................... 546/48

* cited by examiner

*Primary Examiner* — Charanjit Aulakh
(74) *Attorney, Agent, or Firm* — Scott A. Whitaker; BioNeumerik Pharmaceuticals, Inc.

(57) ABSTRACT

The present invention discloses and claims five (5) novel, highly efficient synthetic routes for the total synthesis of enantiomerically-pure (i.e., 99%) 7-(2'-trimethylsilyl)ethyl camptothecin (BNP1350; Karenitecin; Cositecan). These aforementioned synthetic schemes are the first to disclose the total syntheses of 7-(2'-trimethylsilyl)ethyl camptothecin using a highly novel direct, non-linear and convergent synthetic strategy which involves annealing the key C7-(trimethylsilyl)ethyl side chain-bearing A ring key synthons to an enantiomerically-pure tricyclic pyridone; rather than through the conventional methodology which incorporates the C7-(trimethylsilyl)ethyl side chain as the final synthetic step on a totally synthesized camptothecin parent compound. The current novel synthetic approaches reported herein since utilize desirably functionalized A-ring with preinstalled trimethyl silyl ethyl side chain, the aforementioned synthetic methodologies have a wider scope of making wide range of pharmaceutically relevant A-ring substituted BNP1350 analogs by substituting desirably functionalized nitro or protected amino phenyl carboxy A-ring as the starting material.

5 Claims, 2 Drawing Sheets

METHODS FOR THE TOTAL CHEMICAL SYNTHESIS OF ENANTIOMERICALLY-PURE 7-(2'-TRIMETHYLSILYL)ETHYL CAMPTOTHECIN

FIELD OF THE INVENTION

The present invention relates to novel chemical strategies for the total synthesis of enantiomerically-pure 7-(2'-trimethylsilyl)ethyl camptothecin (BNP1350; Karenitecin; Cositecan).

BACKGROUND OF THE INVENTION

I. Camptothecin (CPT) and Initial Clinical Trials

Camptothecin (CPT; IUPAC Nomenclature: (S)-4-Ethyl-4-hydroxy-1H-pyrano[3',':6,7]indolizino[1,2-b]quinoline-3,14(4H,12H)-dione) and certain of its analogs have been shown to possess varying degrees of anti-neoplastic activity. Presently, two CPT analogs (Irinotecan and Topotecan, as discussed below) have been approved for therapeutic use in the United States by the Food and Drug Administration (FDA) and globally in several other territories by other regulatory agencies for various forms of solid neoplasms.

CPT was initially isolated in 1966 by Wall, et al., from *Camptotheca accuminata*, (Nyssaceae family) a Chinese yew. See, Wall, M. E., et al., Plant chemotherapeutic agents. I. The Isolation and Structure of Camptothecin, a Novel Alkaloidal Leukemia and Tumor Inhibitor from *Camptotheca Acuminata. J. Am. Chem. Soc.* 88:3888-3890 (1966)).

The structure of this originally isolated camptothecin (CPT) is shown below:

Camptothecin (CPT)

By the early 1970's, CPT had reached Phase I and Phase II clinical trials and although it was found to possess anti-tumor activity, there were numerous deleterious physiological side-effects associated with its use. The side-effects included, but were not limited to, severe and unpredictable myelosuppression, gastrointestinal toxicity, hemorrhagic cystitis, alopecia, diarrhea, nausea, vomiting and the like. These toxicities, found during early clinical studies, rendered the drug "unmanageable" during this time period. See, Muggia, F. M.; et al., Phase I Clinical Trial of Weekly and Daily Treatment With Camptothecin (NSC-100880): Correlation With Pre-clinical Studies. *Cancer Chemother. Rep.* 56:515-521 (1972); Schaeppi, U., et al., Toxicity of Camptothecin (NSC-100880). *Cancer Chemother. Rep.* 5:25-36 (1974).

In order to demonstrate both the utility and novelty of the present invention, it will be instructive to engage in brief review of the published literature dealing with human clinical trials conducted with administered in a parenteral manner. Physicochemical studies of CPT found that the closed E-ring lactone form of CPT possessed extremely poor solubility in water (i.e., approximately 0.1 μg of drug dissolving in 1 mL of water). In addition, of the two CPT enantiomers, the naturally occurring (S)-isomer was found to be more potent than the (R)-isomer. See, e.g., Motwani, M. V., et al., Flavopiridol (Flavo) Potentiates the SN-38-Induced Apoptosis in Association with Downregulation of Cyclin Dependent Kinase Inhibitor p21waf1/cip1 in HCT116 Cells. *Proc. Am. Assoc. Cancer Res.* 41:32-43 (2000). These different properties of the various analogs are caused by the different chemical substituents on the parent structure of CPT.

Thus, because of its extremely poor water solubility, in order for CPT to be administered in human clinical trials through conventional route of administration protocols, it was initially formulated using sodium hydroxide as its monosodium carboxylate form (open lactone form). It is important to note, that all of these early clinical studies used sodium hydroxide formulations of CPT in order to markedly increase the water solubility (i.e., hydrophilicity) of the molecule to allow sufficient quantities of the agent to be administered parenterally and in some cases orally to patients. The sodium hydroxide formulation of CPT created more water soluble CPT species that permitted clinicians to administer larger concentrations of CPT with smaller medication volumes of administration, thereby allowing sufficiently higher doses of the drug to be administered to cancer subjects undergoing Phase I and Phase II clinical trials. However, it was subsequently established that this formulation resulted in hydrolysis of the lactone E-ring of the camptothecin molecule, thus forming the water soluble carboxylate form of CPT which only possessed approximately one-tenth or less of the anti-tumor potency of the original, non-hydrolyzed lactone form of CPT. The clinical trials performed using the sodium hydroxide-formulated CPT provide to be highly disappointing, due to both the frequently-observed significant systemic toxicities and the lack of anti-neoplastic activity. It was subsequently ascertained that the drug's relative low hydrophilicity, was the most important reason for these side-effects. This low aqueous solubility of CPT in the lactone form greatly limited the practical clinical utility of the drug because prohibitively large volumes of fluid had to be administered to the subject in order to provide an effective dose of the drug. Because of the potent anti-neoplastic activity and poor water solubility of CPT lactone forms and many of its analogs in water, a great deal of effort was directed at generating new CPT lactone analogs that possessed greater aqueous solubility. Water soluble CPT analogs should not exist in large amounts in the open E-ring form but, alternately, should predominantly remain in the closed-ring lactone form, in order to be active. Thus, CPT analogs where equilibrium favors the closed-ring lactone form are desirable for administration.

II. Pharmacological Activity of CPT

Despite these earlier disappointing side-effects, increasing clinical interest in CPT was evoked during the 1980s, as a result of the revelation of its mechanism of action (i.e., Topoisomerase I inhibition). This new information regarding the mechanism of action of CPT analogs served to rekindle the interest in developing new Topo I inhibitors for use as anti-neoplastic drugs and subsequently several research groups began attempting to develop new CPT analogs for cancer therapy. See, Hsiang, Y. H., et al., Camptothecin Induces Protein-Linked DNA Breaks Via Mammalian DNA Topoisomerase I. *J. Biol. Chem.* 260:14873-14878 (1985); Hsiang, Y. H.; Liu, L. F., Identification of Mammalian DNA Topoisomerase I as an Intracellular Target of the Anticancer Drug Camptothecin. *Cancer Res.* 48:1722-1726 (1988); Hsiang, Y. H., et al., Arrest of Replication Forks by Drug-Stabilized Topoisomerase I DNA Cleavable Complexes as a Mechanism of Cell Killing by Camptothecin. *Cancer Res.* 49:5077-5082 (1989).

Several clinically important anticancer drugs kill tumor cells by affecting DNA Topoisomerases. Topoisomerases are essential nuclear enzymes that function in DNA replication and tertiary structural modifications (e.g., overwinding, underwinding, and catenation) which normally arise during replication, transcription, and perhaps other DNA processes. Two major Topoisomerases that are ubiquitous to all eukaryotic cells: (i) Topoisomerase I (Topo I) which cleaves single stranded DNA and (ii) Topoisomerase II (Topo II) which cleaves double stranded DNA. Topoisomerase I is involved in DNA replication; it relieves the torsional strain introduced ahead of the moving replication fork.

Topoisomerase I (Topo I) is a monomeric 100 kDal polypeptide containing 765 amino acids, and is encoded by a gene located on chromosome 20q12-13.2. See, e.g., Creemers, G. J., et al., Topoisomerase I Inhibitors: Topotecan and Irinotecan. *Cancer Treat. Rev.* 20:73-96 (1994); Takimoto, C. H.; Arbuck, S. G. The Camptothecins. *Cancer Chemother and Biother. 2nd edition* (B. L. Chabner, D. L. Longo (eds)), 463-384 (1996). It is an essential enzyme in DNA replication and RNA transcription, and is present in all eukaryotic (including tumor) cells. Since normal DNA is super-coiled, and tightly fitted in the chromosomes, the DNA-replication fork is unable to synthesize new DNA out of this topological constrained DNA. Topo I acts in an ATP-independent fashion, by binding to super-coiled DNA and cleaving a phosphodiester bond, resulting in a single-strand break. At the same time, Topo I forms a covalent reversible adduct between a tyrosine residue at position 723 of Topo I and the 3' end of the single-strand DNA molecule, called the cleavable complex. The DNA molecule is able to rotate freely around the intact single DNA strand, and relaxation of the DNA occurs. After the religation of the cleavage, Topo I dissociates from the DNA. The cleavable complex usually is present for only a short time, just to allow the single uncleaved DNA strand to unwind.

Specifically, it was found that CPT forms a reversible covalent complex comprising: Topo I-CPT-DNA. In brief, the primary mechanism of action of CPT is the inhibition of Topo I by blocking the rejoining step of the cleavage/religation reaction of Topo I, thus resulting in the accumulation of covalent reaction intermediates (i.e., the cleavable complex). CPT-based cellular apoptosis is S-phase-specific killing through potentially lethal collisions between advancing replication forks and Topo I DNA complexes. Two repair responses to Topo I-mediated DNA damage involving covalent modification of Topo I have been identified. The first involves activation of the Ubiquitin/26S proteasome pathway, leading to degradation of Topo I (CPT-induced Topo I down-regulation). The second involves the Small Ubiquitin-like Modifier (SUMO) conjugation to Topo I. These repair mechanisms for Topo I-mediated DNA damage play an important role in determining CPT sensitivity/resistance in tumor cells.

Topo I purified from human colon carcinoma cells or calf thymus has been shown to be inhibited by CPT. CPT, Irinotecan (CPT-11) and an additional Topo I inhibitor, Topotecan, has been in used in clinical trials to treat certain types of human cancer. For the purpose of this invention, CPT analogs include: 7-ethyl-10-[4-(1-piperidino)-1-piperidino]carbonyloxy camptothecin (Irinotecan or CPT-11), 10-hydroxy-7-ethyl camptothecin (HECPT), 9-aminocamptothecin, 10,11 methylenedioxy camptothecin and 9-dimethylaminomethyl-10-hydroxy camptothecin (Topotecan). These CPT analogs use the same mechanism to inhibit Topo I; they stabilize the covalent complex of enzyme and strand-cleaved DNA, which is an intermediate in the catalytic mechanism. These analogs have no binding affinity for either isolated DNA or Topo I but do bind with measurable affinity to the enzyme-DNA complex. The stabilization of the Topo I "cleavable complex" by CPT and analogs is readily reversible.

Topoisomerase II (Topo II) works in a similar way to Topo I, with the difference being that the former enzyme acts ATP-dependently, to cause reversible doublestrand DNA cleavage, in the relaxation of DNA. Direct interference of CPTs with Topo II has not been described. However, it has been reported that Irinotecan (CPT-11) treatment sensitizes some tumor-xenografts in mice to Topo II inhibitors, by increasing the Topo II mRNA expression after 24 and 48 hours. This suggests that combination therapies with Topo I and Topo II targeting chemotherapy for human solid tumors might be valuable. The CPT analogs inhibit the religation reaction of Topo I by selectively inducing a stabilization of the cleavable complexes at Topo I sites bearing a guanine residue at the 5'-terminus of the enzyme mediated breaks. See, e.g., Svejstrup, J. Q., et al., Technique for Uncoupling the Cleavage and Religation Reactions of Eukaryotic Topoisomerase I. The Mode of Action of Camptothecin at a Specific Recognition Site. *J. Mol. Biol.* 222:669-678 (1991); Jaxel, C., et al., Effect of Local DNA Sequence on Topoisomerase I Cleavage in the Presence or Absence of Camptothecin. *J. Biol. Chem.* 266: 20418-20423 (1991); Tanizawa, A., et al., Induction of Cleavage in Topoisomerase I c-DNA by Topoisomerase I Enzymes From Calf Thymus and Wheat Germ in the Presence and Absence of Camptothecin. *Nucl. Acids Res.* 21:5157-5166 (1994). Although this stabilization in itself is reversible, an irreversible doublestrand break occurs when a replication fork meets a cleavable complex. The higher the levels of Topo I, the higher the frequency of cleavable complexes, and the higher the number of DNA breaks. These breaks may lead to cell cycle arrest in the S/G2-phase, activation of apoptosis pathways, and finally to cell death. See, e.g., Hsiang, Y. H., et al., Arrest of Replication Forks by Drug-Stabilized Topoisomerase I DNA Cleavable Complexes as a Mechanism of Cell Killing by Camptothecin. *Cancer Res.* 49:5077-5082 (1989). As a result of this, Topo I inhibitors are only lethal in the presence of ongoing DNA replication or RNA transcription. See, e.g., D'Arpa, P., et al., Involvement of Nucleic Acid Synthesis in Cell Killing Mechanisms of Topoisomerase I Poisons. *Cancer Res.* 50:6919-6924 (1990). S-phase synchronized cells appeared to be much more sensitive to Topo I inhibitors, compared to G1- or G2/M-cells, suggesting an S-phase specific cytotoxicity for this type of drugs. See, e.g., Takimoto, C. H., et al., Phase I and Pharmacologic Study of Irinotecan Administered as a 96-Hour Infusion Weekly to Adult Cancer Patients. *J. Clin. Oncol.* 18:659-667 (2000). In colon, prostate, ovary and esophagus tumors, elevated Topo I levels have been found, whereas in kidney tumors and non-Hodgkin lymphomas this was not the case. See, e.g., Van der Zee, A., et al., P-glycoprotein Expression and DNA Topoisomerase I and II Activity in Benign Tumors of the Ovary and in Malignant Tumors of the Ovary, Before and After Platinum/Cyclophosphamide Chemotherapy. *Cancer Res.* 51: 5915-5920 (1991). Recent investigations have indicated that Irinotecan and Topotecan are also inhibitors of angiogenesis, a property that might contribute to their chemotherapeutic activity. Neovascularization has been positively correlated with increasing invasion and metastases of various human tumors. In mice cornea models, anti-angiogenic effects of some CPTs, including Irinotecan (CPT-11), were studied. Angiogenesis was induced by fibroblast growth factor, but by increasing the dose of Irinotecan CPT-11, the area of angiogenesis in the tumor decreased, following a negative, almost exponential, curve. At dose levels of 210 mg/kg a significant reduction of neovascularization was observed.

Although CPT and the aforementioned CPT analogs have no discernable direct effects on Topo II, these CPT analogs are believed to stabilize the "cleavable complex" in a manner analogous to the way in which epipodophyllotoxin glycosides and various anthracyclines inhibit Topo II.

Inhibition of Topo I by CPT and analogs induces protein-associated-DNA single-strand breaks. Virtually all of the DNA strand breaks observed in vitro cells treated with CPT are protein linked. However, an increase in unexplained protein-free breaks can be detected in L1210 cells treated with CPT. The analogs appear to produce identical DNA cleavage patterns in end-labeled linear DNA. It has not been demonstrated that CPT or CPT analogs cleaves DNA in the absence of the Topo I enzyme.

III. Cell Cycle-Specific Activity of Camptothecin

The activity of CPT is cell cycle-specific. The greatest quantitative biochemical effect observed in cells exposed to CPT is DNA single-strand breaks that occur during the S-phase. Because the S-phase is a relatively short phase of the cell cycle, longer exposure to the drugs results in increased cell killing. Brief exposure of tumor cells to the drugs produces little or no cell killing, and quiescent cells are refractory. These aforementioned results are likely due to two factors:
 (i) This class of drugs inhibits the normal activity of Topo I, reversibly. Although they may produce potentially lethal modifications of the DNA structure during DNA replication, the DNA strand breaks may be repaired after washout of the drug; and
 (ii) Cells treated with Topo I inhibitors, such as CPT tend to stay in $G_0$ of the cell cycle until the drug is removed and the cleaved DNA is repaired. Inhibitors of these enzymes can affect many aspects of cell metabolism including replication, transcription, recombination, and chromosomal segregation.

IV. Karenitecin/BNP1350

Highly lipophilic camptothecin derivatives (HLCDs), particularly those containing silicon-based moieties, are effective anti-cancer drugs. One of the most noted of the silicon-containing HLCDs is Karenitecin® (also known as BNP1350, Cositecan; 7-(2'-trimethylsilyl)ethyl camptothecin; IUPAC Nomenclature: (4S)-4-ethyl-4-hydroxy-11-[2-(trimethylsilyl)ethyl]-1H-pyrano[3':4': 6,7]indolizino[1,2-b]quinoline-3,14(4H,12H)-dione)), which is currently in Phase 3 human clinical trials in the United States and internationally. Karenitecin possess the generic structural formula illustrated, below:

Wherein, $R_1$, $R_2$, $R_3$=methyl (—$CH_3$) functional groups covalently-bound to the silicon-containing side chain (bound to C7 on the B-ring) of the Karenitecin molecule.

Karenitecin and its various analogs disclosed and claimed in the present invention, in a non-limiting manner, represent a novel class of chemotherapeutic compounds that have exhibited potent antineoplastic activity against common types of cancer including but not limited to cancers of the lung, breast, prostate, pancreas, head and neck, ovary, colon, as well as melanoma. While Karenitecin (and analogs thereof) possesses Topoisomerase I inhibitory activity similar to that of other camptothecin derivatives, it also possess novel structural modifications that are rationally designed for superior bioavailability and tissue penetration, while concomitantly avoiding untoward metabolism and drug resistance mechanisms which are common in human and other mammalian cancers.

It may be ascertained from pharmacological and biochemical data, that many of the previously synthesized camptothecin analogs possess a number of inherent limitations which markedly decreases their usefulness as anti-cancer agents. In contrast, Karenitecin is a highly lipophilic camptothecin derivative characterized by substantial lactone stability and long plasma half-life. In vitro studies conducted on a panel of over twenty (20) human cancer cell lines indicate that Karenitecin is significantly more potent antitumor agent than either Topotecan or SN-38, the active metabolite of Irinotecan. Equilibrium dialysis studies with human plasma demonstrated that Karenitecin is 98 to 99% protein-bound. The free drug concentration in blood plasma is generally considered to be the pharmacologically active form in clinical pharmacology.

Karenitecin is potentially significantly less toxic than previously disclosed camptothecin derivatives. Moreover, Karenitecin does not undergo A-ring or B-ring glucuronidation (and implicitly deglucuronidation). The lack of glucuronidation decreases deleterious physiological side-effects (e.g., diarrhea, leukopenia) and may also mitigate substantial interpatient variability in drug levels of the free metabolite and its glucuronide conjugate. Karenitecin and its analogs are not prodrugs, requiring metabolic activation.

Thus, Karenitecin: (i) possesses potent antitumor activity (i.e., in nanomolar or sub-nanomolar concentrations) for inhibiting the growth of human and animal tumor cells in vitro; (ii) is a potent inhibition of Topoisomerase I; (iii) lacks of susceptibility to MDR/MRP drug resistance; (iv) require no metabolic drug activation: (v) lacks glucuronidation of the A-ring or B-ring; (vi) reduces drug-binding affinity to plasma proteins; (vii) maintains lactone stability; (viii) maintains drug potency; and (ix) possesses a low molecular weight (e.g., MW<600).

SUMMARY OF THE INVENTION

The present invention disclosed and claimed herein have many attributes and embodiments including, but not limited to, those set forth or described or referenced in this Summary. It is not intended to be all-inclusive and the inventions described and claimed herein are not limited to or by the features or embodiments identified in this Summary, which is included for purposes of illustration only and not restriction.

In one embodiment, the present invention discloses a process for the total chemical synthesis of Karenitecin (also known as BNP1350, Cositecan; 7-(2'-trimethylsilyl)ethyl camptothecin; IUPAC Nomenclature: (4S)-4-ethyl-4-hydroxy-11-[2-(trimethylsilyl)ethyl]-1H-pyrano[3':4':6,7]indolizino[1,2-b]quinoline-3,14(4H,12H)-dione)). In this embodiment, the starting material is commercially available, cost effective 2-nitrobenzaldehyde. The first step of the total synthetic process involve the Grignard addition of 2-(trimethylsilyl)vinylmagnesium bromide to the aforementioned starting material, followed by oxidation of this intermediate to produce vinyl aryl ketone. Industrially scalable hydrogenation in presence of Pd/C produced the key A-ring intermediate 1-(2-amino-phenyl)-3-trimethylsilanyl-propan-1-one. Friedlander condensation of 1-(2-amino-phenyl)-3-trimethylsilanyl-propan-1-one with commercial available enantiomerically pure CDE ring intermediate (tricyclic pyridone) gave the desired BNP1350 product.

In another embodiment, the present invention discloses a process for the total chemical synthesis of Karenitecin (also known as BNP1350, Cositecan). In this embodiment, the starting reagent is commercially available, cost-effective N-Boc-aniline. The synthesis process first included treatment of N-Boc-aniline with tert-butyl lithium, followed by addition to methoxymethyl(3-trimethylsilyl)propionamide to generate 243% trimethylsilylpropionyl)-N-Boc-aniline as A ring key intermediate. Friedlander condensation of (7-trimethylsilylpropionyl)-N-Boc-aniline with commercial available chiral CDE ring intermediate gave the desired BNP1350 product.

In still another embodiment, the present invention discloses a process for the total chemical synthesis of Karenitecin (also known as BNP1350, Cositecan). In this embodiment, the starting reagent is commercially available, cost effective N-Boc-2-iodoaniline. The synthesis process includes first coupling N-Boc-2-iodoaniline with ethynyltrimethylsilane and followed by hydrogenation in presence of Pd/C to generate 2-(3'-trimethylsilylpropionyl)-N-Boc-aniline to obtain the A ring key intermediate. The Friedlander condensation of 2-(3'-trimethylsilylpropionyl)-N-Boc-aniline with the commercially available chiral CDE ring moiety gave the desired BNP1350 (Karenitecin; Cositecan) product.

In yet another embodiment, the present invention discloses a process for the total chemical synthesis of Karenitecin (also known as BNP1350, Cositecan). In this embodiment, the starting reagent is commercially available, cost effective ethynyltrimethylsilane to which solutions of n-butullithium and o-nitrobenzaldehyde were added to form 1-(2-nitrophenyl)-3-trimethylsilyl-2-propyn-1-ol. Oxidation of propyn-1-ol with manganese dioxide generated 2-(3'-trimethylsilylpropiolyl)-nitrobenzene, which was concerted to the key A-ring intermediate 1-(2-amino-phenyl)-3-trimethylsilanyl-propan-1-one by hydrogenation in presence of Pd/C. The Friedlander condensation of 1-(2-amino-phenyl)-3-trimethylsilanyl-propan-1-one with commercial available chiral CDE ring moiety gave the desired BNP1350 product.

In a further embodiment, the present invention discloses a process for the total chemical synthesis of Karenitecin (also known as BNP1350, Cositecan). In this embodiment, the starting reagent is commercially available, cost effective 2-nitrobenzoic acid. The synthesis process first included activation of 2-nitrobenzoic acid to the more active 2-nitrobenzoyl chloride, followed by Friedel-Craft alkynylation of this crude acid chloride with bis(trimethylsilyl)acetylene to generate 1-phenyl-3-trimethylsilyl-propynone. Subsequent hydrogenation of the previous intermediate in presence of Pd/C produces the key A-ring intermediate synthon 1-(2-amino-phenyl)-3-trimethylsilanyl-propan-1-one, the crystallization of which in presence of 1 N HCl gave 1-(2-amino-phenyl)-3-trimethylsilanyl-propan-1-one salt. The Friedlander condensation of 1-(2-amino-phenyl)-3-trimethylsilanyl-propan-1-one salt with the commercially available chiral CDE ring moiety gave the desired BNP1350 product.

DESCRIPTION OF THE FIGURES

Panel A shows the HPLC peaks for (R)-BNP1350 and (S)-BNP1350 which was synthesized using the aforementioned protocol set forth in U.S. Pat. No. 7,030,243.

Panel B shows the HPLC peaks for results (S)-BNP1350 which was synthesized using Synthesis Scheme 1 disclosed in the present patent application. As one can ascertain, the value for the natural (S)-BNP1350 (Panel A; 15.012 minutes) and that for synthetic (S)-BNP1350 (Panel B; 14.699 minutes) are extremely close.

DETAILED DESCRIPTION OF THE INVENTION

The embodiments herein described are not intended to be exhaustive, or to limit the invention to the precise forms disclosed. They are chosen to best illustrate the principles of the invention, and its application and practical use to best enable others skilled in the art to follow its teachings.

As previously disclosed, camptothecin is isolated from its natural source *Camptotheca accuminata*, (Nyssaceae family) a Chinese yew (see, Wall, M. E., et al., Plant chemotherapeutic agents. I. The Isolation and Structure of Camptothecin, a Novel Alkaloidal Leukemia and Tumor Inhibitor from Camptotheca Acuminata. *J. Am. Chem. Soc.* 88:3888-3890 (1966)). As this species of Chinese yew grows only in a single southeastern province of China, any substantial or long-term climatic change and/or insect, mold, or fungal infestation could cause a marked reduction in the number of viable trees, with an associated concomitant reduction in the amount of camptothecin capable of being harvested. Recently two other plant species, *Nothapodytes nimmoniana* and *Nothapodytes foetida*, from India were identified as alternate natural sources for the isolation of camptothecin (CPT), the member of monoterpene indole alkaloid. It is also interesting to note, that the camptothecin and its congeners content varies in various parts of the aforementioned tree species that include the isolating parts as roots, bark, leaves and seeds.

While BNP1350 (Karenitecin; Cositecan) can be synthesized through a high yielding, convergent semi-synthetic methodology starting with naturally-occurring camptothecin, an abundant and reliable source of such naturally-occurring camptothecin has heretofore been a continuous concern in the pharmaceutical industry. Therefore robust, cost effective, and industrially scalable synthetic routes for the total synthesis of BNP1350, without dependence upon the isolation of naturally-occurring camptothecin, would have immense value.

Although there are several camptothecin total syntheses synthetic schemes known in literature, they are generally restricted to academic use/interest and possess extremely limited value for use in the pharmaceutical industry, as these aforementioned synthetic routes are not scalable and/or involve the use of expensive reagents or intermediates in the synthesis.

The present invention discloses and claims five (5) novel, highly efficient synthetic routes for the total chemical synthesis of enantiomerically-pure (i.e., 0.99%) BNP1350 (Karenitecin; Cositecan). These aforementioned synthetic methods are the first to disclose the total syntheses of BNP1350 using a highly novel direct and convergent non-linear synthetic strategy which involves annealing the key C7-(trimethylsilyl) ethyl side chain-bearing key A ring synthons to an enantiomerically-pure commercially available tricyclic pyridone; rather than through the conventional methodology which incorporates the C7-(trimethylsilyl)ethyl side chain as the final synthetic step on a totally synthesized camptothecin parent compound. The current novel synthetic approaches reported herein since utilize desirably functionalized A-ring with preinstalled trimethyl silyl ethyl side chain, the aforementioned synthetic methodologies have a wider scope of making wide range of pharmaceutically relevant A-ring substituted BNP1350 analogs by substituting desirably functionalized nitro or protected amino phenyl carboxy A-ring as the starting material.

Specific Examples of Schemes for the Total Synthesis of BNP1350 (Karenitecin)

General Procedures:

All reactions were run under an inert atmosphere of dry argon or nitrogen. Commercial reagents were used without further purification. $^1$H and $^{13}$C NMR spectra were obtained using a Varian Gemini 300 MHz spectrometer and deuterated chloroform as the solvent, unless otherwise specified. Chemical shifts are reported in parts per million (ppm) downfield from tetraethylsilane.

HPLC Method:

The reaction mixtures and the purities of compounds were monitored by a Waters 2695 HPLC instrument. It employs XTerra C18 reversed phase column (4.6×250 mm) with Waters 474 Scanning Fluorescence detector ($\lambda_{ex}$ 370 nm; $\lambda_{em}$ 430 nm), using a gradient of 10-90% of acetonitrile in 0.05% formic acid at a flow rate of 1 mL/min.

1. Synthesis Scheme One

Scheme 1 illustrates the first process of the present invention employed to synthesize BNP1350. As shown, the starting reagent was commercially available, cost effective 2-nitrobenzaldehyde (1). The process includes first 2-(trimethylsilyl)vinylmagnesium bromide addition and following oxidation of the crude to produce vinyl aryl ketone (2). Hydrogenation in presence of Pd/C produced the key A-ring moiety 1-(2-amino-phenyl)-3-trimethylsilanyl-propan-1-one (3), and this intermediate (3) was pure enough to be used directly for the next step without purification. The Friedlander condensation of 1-(2-amino-phenyl)-3-trimethylsilanyl-propan-1-one with commercial available CDE ring moiety (4) gave the desired BNP1350 (Karenitecin; Cositecan) product with a 90% yield.

1-(2-Nitrophenyl)-3-trimethylsilanyl-propenone (2)

To a mixture of 2-bromovinyltrimethylsilane (0.5 g) and magnesium turning (0.1 g) in tetrahydrofuran (THF; 2.5 mL) was added a piece of iodine. The mixture was refluxed for one hour and diluted with 2.5 mL of THF. The reaction was then cooled to room temperature, producing the requisite 2-(trimethylsilyl)vinylmagnesium bromide solution. The resulted Grignard was added to the solution of 2-nitrobenzoaldehyde (281 mg) in THF (2.5 mL) at −30° C. The reaction mixture was stirred at −30° C. for one hour. 4% ammonium chloride solution was then added. The aqueous phase was extracted with 5 mL of ethyl acetate a total of 3-times (EtOAc, 3×5 mL). The combined organic phases were filtered and the filtrate was evaporated under reduced pressure to yield brown oil.

The crude product from the previous step was dissolved in dichloromethane (CH$_2$Cl$_2$; 8 mL). 2,2,6,6-Tetramethyl-1-piperidinyloxy (TEMPO, 2 mg), sodium bromide (96 mg) and water (4 mL) were added. To this mixture, a solution of sodium hypochlorite (4.81% in water, 2.2 g) and sodium bicarbonate (104 mg) in water (4 mL) was added slowly. The reaction was stirred at room temperature for one hour. Another portion of sodium hypochlorite (4.81% in water, 4.3 g) and sodium bicarbonate (372 mg) in water (5 mL) was then added. The reaction was continued for another two hours. Aqueous phase was extracted with 10 mL of dichloromethane a total of 3-times (3×10 mL). The combined organic phases were filtered and the filtrate was evaporated under reduced pressure. The crude product was subjected to silica gel chromatography (10% ethyl acetate in hexane; SiO$_2$) to produce the desired 1-(2-nitrophenyl)-3-trimethylsilanyl-propenone (2) (121 mg; 56% yield).

$^1$H NMR (300 Hz, CDCl$_3$) δ 8.13 (dd, 1H, J=8.0, 1.2 Hz), 7.77-7.71 (m, 1H), 7.66-7.61 (m, 1H), 7.44 (dd, 1H, J=7.5, 1.5 Hz), 6.71 (dd, 2H, J=26.25, 19.2 Hz), 0.125 (s, 9H).

1-(2-Amino-phenyl)-3-trimethylsilanyl-propan-1-one (3)

The mixture of 1-(2-nitrophenyl)-3-trimethylsilanyl-propenone (2) (98 mg) and palladium on charcoal (5%; 49 mg) in ethyl acetate (4 mL) was stirred at room temperature under hydrogen balloon pressure for sixteen hours. After filtration through Celite, the filtrate was evaporated to dryness under reduced pressure to yield 1-(2-amino-phenyl)-3-trimethylsilanyl-propan-1-one (3) as light-yellow oil, which was pure enough to use in the next synthesis step without further purification:

1H NMR (300 Hz, CDCl$_3$) δ 7.74 (dd, 1H, J=8.4, 1.2 Hz), 7.29-7.24 (m, 1H), 6.69-6.63 (m, 2H), 2.94-2.88 (m, 2H), 0.93-0.87 (m, 2H), 0.058 (s, 9H).

(4S)-4-ethyl-4-hydroxy-11-[2-(trimethylsilyl)ethyl]-1H-pyrano[3':4':6,7]indolizino[1,2-b]quinoline-3,14(4H,12H)-dione (BNP1350)

To a solution of 1-(2-amino-phenyl)-3-trimethylsilanyl-propan-1-one (3) (34 mg) and CDE ring moiety (4) (24 mg) in acetic acid (0.5 mL) and toluene (1 mL) was added p-toluenesulfonic acid (1 mg). The reaction solution was stirred for 20 hours at 100° C. After cooling to room temperature, the reaction solution was concentrated under reduced pressure and the residue was washed with hexane (10 mL), water (10 mL), and a mixture of acetone (5 mL) and hexane (5 mL). The yellow solid was evaporated to dryness in vacuo to yield 39 mg (98% Yield) of BNP1350 (Karenitecin; Cositecan; 7-(2'-trimethylsilyl)ethyl camptothecin; IUPAC Nomenclature: (4S)-4-ethyl-4-hydroxy-11-[2-(trimethylsilyl)ethyl]-1H-pyrano[3':4':6,7]indolizino[1,2-b]quinoline-3,14(4H,12H)-dione).

$^1$H NMR (300 MHz, CDCl$_3$) δ 8.24 (d, 1H, J=8.4 Hz), 8.05 (d, 1H, J=7.5 Hz), 7.82 (t, 1H, J=7.2 Hz), 7.71-7.66 (m, 2H), 5.77 (d, 1H, J=16.2 Hz), 5.33 (d, 1H, J=16.2 Hz), 5.26 (s, 2H), 3.73 (s, 1H), 3.15-3.09 (m, 2H), 1.96-1.86 (m, 2H), 1.03 (t, 3H, J=7.5 Hz), 0.91-0.98 (m, 2H), 0.19 (s, 9H).

$^{13}$C NMR (300 MHz, CDCl$_3$) δ 174.15, 157.91, 152.17, 150.41, 149.75, 147.34, 147.24, 130.98, 130.20, 127.84, 126.83, 126.28, 123.49, 118.67, 98.21, 73.01, 66.59, 49.48, 31.86, 24.32, 18.00, 8.04, −1.65.

MS: 449 (M+1); Chiral Purity: 100% ee.

$^1$H and $^{13}$C NMR Analysis

In order to ascertain any differences in the BNP1350 produced by Synthesis Scheme 1 versus that produced as set forth in U.S. Pat. No. 7,030,243 (which has the same Assignee as the present patent application) entitled: "Preparation of Camptothecin Derivatives" using camptothecin isolated from a natural source, $^1$HH and $^{13}$C NMR Analysis was performed.

$^1$H NMR and $^{13}$C NMR spectrums of BNP1350 prepared via Synthesis Scheme 1 were consistent with BNP1350 made using naturally-derived camptothecin.

NMR Analysis of BNP1350 from Naturally-Derived Camptothecin $^1$H NMR (300 MHz, CDCl$_3$) δ 8.23 (d, 1H, J=8.4 Hz), 8.04 (d, 1H, J=8.4 Hz), 7.80 (t, 1H, J=7.2 Hz), 7.69-7.64 (m, 2H), 5.76 (d, 1H, J=16.5 Hz), 5.33 (d, 1H, J=16.5 Hz), 5.24 (s, 2H), 3.14-3.08 (m, 2H), 1.96-1.82 (m, 2H), 1.04 (t, 3H, J=7.4 Hz), 0.90-0.96 (m, 2H), 0.18 (s, 9H).

$^{13}$C NMR (75 MHz, CDCl$_3$) δ 174.07, 157.82, 151.96, 150.31, 149.47, 147.39, 147.11, 130.77, 130.26, 127.84, 126.75, 126.24, 123.45, 118.68, 98.35, 72.99, 66.54, 49.47, 31.80, 24.35, 17.99, 8.08, −1.63.

NMR analysis of BNP1350 from Synthesis Scheme 1

$^1$H NMR (300 MHz, CDCl$_3$) δ 8.24 (d, 1H, J=8.4 Hz), 8.05 (d, 1H, J=7.5 Hz), 7.82 (t, 1H, J=7.2 Hz), 7.71-7.66 (m, 2H), 5.77 (d, 1H, J=16.2 Hz), 5.33 (d, 1H, J=16.2 Hz), 5.26 (s, 2H), 3.73 (s, 1H), 3.15-3.09 (m, 2H), 1.96-1.86 (m, 2H), 1.03 (t, 3H, J=7.5 Hz), 0.91-0.98 (m, 2H), 0.19 (s, 9H).

$^{13}$C NMR (300 MHz, CDCl$_3$) δ 174.15, 157.91, 152.17, 150.41, 149.75, 147.34, 147.24, 130.98, 130.20, 127.84, 126.83, 126.28, 123.49, 118.67, 98.21, 73.01, 66.59, 49.48, 31.86, 24.32, 18.00, 8.04, −1.65.

HPLC-Based BNP1350 Chirality Analysis

In order to ascertain any differences in the chirality of BNP1350 produced by Synthesis Scheme 1 versus BNP1350 produced as set forth in U.S. Pat. No. 7,030,243 (which has the same Assignee as the present patent application) entitled: "Preparation of Camptothecin Derivatives", which uses camptothecin isolated from a natural source. The conditions used for the HPLC-based chirality analysis were as follows:

HPLC Condition for Chirality Check: (022812)

(1) Column: Chiral-AGP column (ChromTech, 4.0×100 mm)

(2) Mobile Phase: 11% Acetonitrile and 89% 10 nM Ammonium Acetate

(3) Flow Rate: 1.0 mL/min (4) Column Temperature: 30° C.

(5) Detection: PDA @ 254 nm (6) The separation was run with a WATERS (2695) HPLC-(2996) UV system (a GMP certified analytical instrument at 022712)

Figure 1:
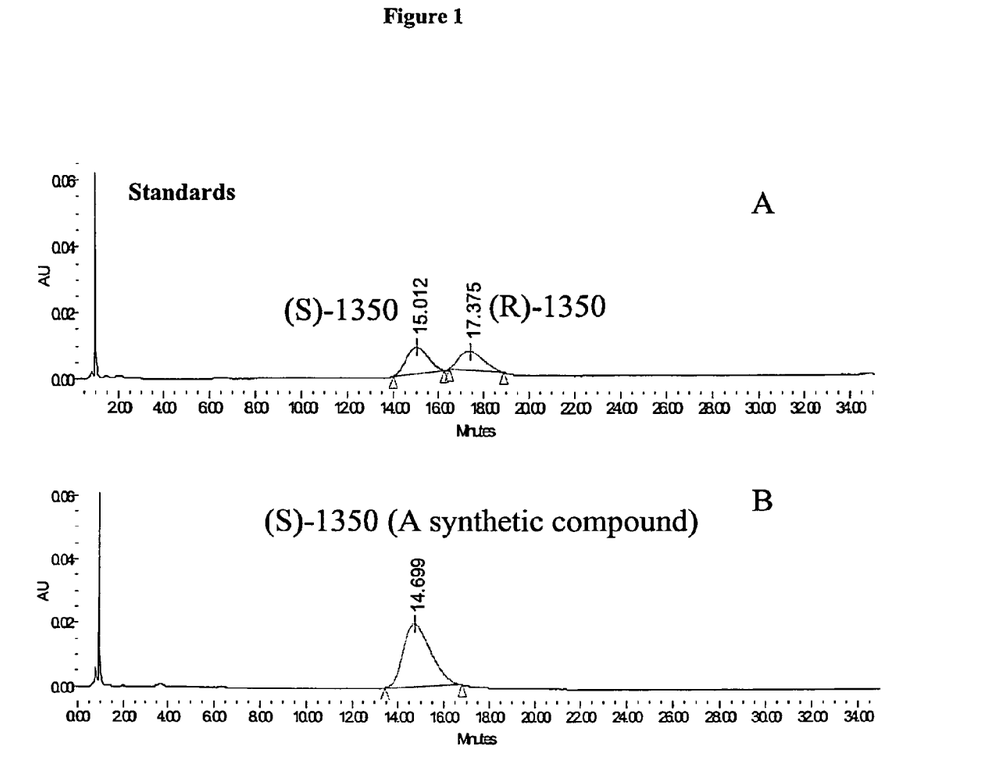
FIG. 1 illustrates the results of the HPLC-based chirality analysis.

FIG. 1 illustrates the results of the HPLC-based chirality analysis. Panel A shows the HPLC peaks for (R)-BNP1350 and (S)-BNP1350 which was synthesized using the aforementioned protocol set forth in U.S. Pat. No. 7,030,243. Panel B shows the HPLC peaks for results (S)-BNP1350 which was synthesized using Synthesis Scheme 1 disclosed in the present patent application. As one can ascertain, the value for the natural (S)-BNP1350 (Panel A; 15.012 minutes) and that for synthetic (S)-BNP1350 (Panel B; 14.699 minutes) are extremely close.

densation of 2-(3'-trimethylsilylpropionyl)-N-Boc-aniline (7) with commercially available CDE ring moiety (4) gave the desired BNP1350 (Karenitecin; Cositecan) product with excellent yield.

Methoxymethyl(3-trimethylsilyl)propionamide (6)

A round-bottomed flask was charged with 3-trimethylsilylpropionic acid (500 mg). Oxalyl chloride (1.45 mL) was added and the reaction mixture was stirred at room temperature for 1.5 hours. The excess of oxalyl chloride was removed under reduced pressure. The acid chloride was used without further purification. Acid chloride and N,O-dimethylhydroxylamine hydrochloride (433 mg) was dissolved in anhydrous methylene chloride. The solution was cooled to 0° C. and pyridine (830 µL) was added. The mixture was stirred at ambient temperature for 2 hours and evaporated in vacuo. The residue was portioned between brine and methylene chloride. The organic layer was dried over sodium sulfate and concentrated in vacuo. The crude amide was purified by silica gel column and produced a yield of 612 mg (94%).

$^1$H NMR (300 MHz, CDCl$_3$) δ 3.69 (3H, s), 3.19 (3H, s), 2.42-2.35 (2H, m), 0.86-0.81 (2H, m), 0.024 (9H, s).

$^{13}$C NMR (75.4 MHz, CDCl$_3$) δ 179.45, 61.40, 26.67, 19.91, 11.39, −1.67.

2-(3'-Trimethylsilylpropionyl)-N-Boc-aniline (7)

A solution of N-Boc-aniline (100 mg) in anhydrous diethyl ether was cooled to −20° C., treated with 2.5 equivalents of tert-butyllithiun (1.7 M in pentane; 1.3 mM), stirred for 2 hours at −10° C., and then for 1 hour at 0° C. After the mixture was cooled to −76° C., an ethereal solution of 1.1 equivalents of the Weinreb amide (6) (109 mg) was added and the resulting mixture allowed to slowly warm to room temperature, stirred overnight, and quenched with 0.1N hydrochloric acid. The mixture was then extracted with dichloromethane. The organic solution was dried over sodium sulfate and evaporated under vacuum. The crude material was purified by chromatography on silica gel and produced a total yield of 103 mg (62%).

$^1$H NMR (300 MHz, CDCl$_3$) δ 8.49-8.46 (1H, m), 7.89-7.86 (1H, m), 7.54-7.48 (1H, m), 7.06-7.00 (1H, m), 2.99-2.94 (2H, s), 1.53 (9H, s), 0.93-0.87 (2H, m), 0.065 (9H, s).

$^{13}$C NMR (75.4 MHz, CDCl$_3$) δ 205.64, 153.41, 142.04, 134.78, 130.81, 121.19, 121.11 119.59, 80.63, 34.74, 28.52, 11.61, −1.59.

BNP1350

A-Ring (7) (20 mg) and CDE-ring (4) (16 mg) were dissolved in a mixture of acetic acid and toluene (1 mL; 1:1 v/v). Toluensulfonic acid (1 mg) was added and the reaction mixture was stirred at 100° C. for 24 hours. The reaction mixture was allowed to cool to room temperature and concentrated under reduced pressure. The residue was then washed 2-times with hexane (2×10 mL) and dried under vacuum. The crude material was purified by silica gel column with a yield of 27 mg (96%). The spectral data were confirmed to be identical to commercially BNP1350 (Karenitecin; Cositecan).

Synthesis Scheme 2 illustrates the second process of the present invention employed to synthesize BNP1350. As shown, the starting reagent was commercially available, cost-effective N-Boc-aniline (5). The synthesis process includes first treatment of N-Boc-aniline (5) with tert-butyl lithium and followed by addition to the freshly-made methoxymethyl (3-trimethylsilyl)propionamide (6) to generate 243% trimethylsilylpropionyl)-N-Boc-aniline (7). The Friedlander con-

3. Synthesis Scheme Three

Scheme 3 illustrates the third process of the present invention employed to synthesize BNP1350. As shown, the starting reagent was commercially available cost effective N-Boc-2-iodoaniline (8). The process includes first coupling N-Boc-2-iodoaniline (8) with ethynyltrimethylsilane and followed by hydrogenation in presence of Pd/C to generate 2-(3'-trimethylsilylpropionyl)-N-Boc-aniline (7). The Friedlander condensation of 2-(3'-trimethylsilylpropionyl)-N-Boc-aniline (7) with the commercially available CDE ring moiety (4) gave the desired BNP1350 (Karenitecin; Cositecan) product.

1-(2-N-Boc-Amino)-3-trimethylsilylpropynone (9)

Into a round-bottomed flask was placed: N-Boc-2-iodo aniline (50 mg), ethynyltrimethylsilane (27 µL), tris(dibenzylideneacetone)dipalladium (15 mg), 1,1'-bis(diphenylphosphino)ferrocene (8.9 mg), triethylamine (45 µL), and tetrahydrofuran (THF). The flask was placed into the "Parr Instrument" reactor under a carbon monoxide (CO) atmosphere (100 psi). The reaction mixture was stirred at room temperature for 48 hours. The carbon monoxide (CO) pressure was released and the reaction mixture was poured into a separatory funnel containing methylene chloride and 0.1N muriatic acid. The aqueous phase was extracted with methylene chloride, and the combined organic phases were dried over sodium sulfate and evaporated under reduced pressure. The crude material was purified by chromatography on silica gel and provided a yield of 17 mg (33%).

$^1$H NMR (300 MHz, CDCl$_3$) δ 10.69 (1H, s), 8.48-8.45 (1H, m), 8.28-8.26 (1H, m), 7.59-7.53 (1H, m), 7.11-7.05 (1H, m), 1.53 (9H, s), 0.33 (9H, s).

$^{13}$C NMR (75.4 MHz, CDCl$_3$) δ 180.66, 153.15, 143.04, 136.13, 135.02, 121.31 118.84, 101.93, 101.03, 81.03, 28.47, −0.50.

2-(3'-Trimethylsilylpropionyl)-N-Boc-aniline (7)

1-(2-N-Boc-Amino)-3-trimethylsilylpropynone (50 mg) was dissolved in ethyl acetate (3 mL). Palladium on carbon (5 mg) was added and the reaction mixture was placed under a hydrogen atmosphere provided by a balloon. The reaction mixture was stirred at room temperature for 6 hours. After completion of the reaction, the palladium on carbon was filtered off using a Celite pad and the solution was concentrated under vacuum. The crude material was purified by silica gel column and gave a yield of 46 mg (92%).

$^1$H NMR (300 MHz, CDCl$_3$) δ 8.49-8.46 (1H, m), 7.89-7.86 (1H, m), 7.54-7.48 (1H, m), 7.06-7.00 (1H, m), 2.99-2.94 (2H, s), 1.53 (9H, s), 0.93-0.87 (2H, m), 0.065 (9H, s).

$^{13}$C NMR (75.4 MHz, CDCl$_3$) δ 205.64, 153.41, 142.04, 134.78, 130.81, 121.11, 119.59, 80.63, 34.74, 28.52, 11.61, −1.59.

BNP1350

A-Ring (20 mg, 0.062 mM) and CDE-ring (16 mg, 0.062 mM) were dissolved in a mixture of acetic acid and toluene (1 mL; 1:1 v/v). Toluensulfonic acid (1 mg) was added and the reaction mixture was stirred at 100° C. for 24 hours. The reaction mixture was cooled to room temperature and concentrated under reduced pressure. The residue was washed 2-times with hexane (2×10 mL) and dried under vacuum. The crude material was purified by silica gel column and provided a yield of 27 mg (96%). The spectral data was shown to be identical to that obtained for commercially available BNP1350.

4. Synthesis Scheme Four ylsilanyl-propan-1-one (3) with the commercial available CDE ring moiety (4) gave the desired BNP1350 product.

1-(2-Nitrophenyl)-3-trimethylsilyl-2-propyn-1-ol (10)

Into a round-bottomed flask was placed ethynyltrimethylsilane (4.90 mL), and tetrahydrofuran (THF) and was cooled to −76° C. A solution of 2.0 M n-butullithium in hexane (15.8 mL) was added dropwise. The reaction mixture was stirred at −76° C. for 30 minutes and a solution of o-nitrobenzaldehyde (3.0 g) in anhydrous THF was added. The reaction mixture was stirred at −76° C. for 60 minutes, and quenched with water. The reaction mixture was warmed up to room temperature and THF was removed under vacuum. The aqueous phase was extracted with ethyl acetate. The combined organic phases were dried over sodium sulfate and evaporated to dryness. The crude material was purified by chromatography on silica gel giving a yield of 4.3 grams (87%).

$^1$H NMR (300 MHz, CDCl$_3$) δ 7.97-7.92 (2H, m), 7.71-7.65 (1H, m), 7.54-7.49 (1H, m), 5.97 (1H, s), 0.19 (9H, s).

$^{13}$C NMR (75.4 MHz, CDCl$_3$) δ 135.24, 133.94, 129.81, 129.58, 125.26, 102.54, 62.04, −0.11.

2-(3'-Trimethylsilylpropiolyl)-nitrobenzene (11)

1-(2-Nitrophenyl)-3-trimethylsilyl-2-propyn-1-ol (5.0 g) was dissolved in dichloromethane (30 mL). To the solution manganese dioxide (8.7 g) was added. The reaction mixture was then stirred at room temperature for 24 hours. After completion of the reaction, the manganese dioxide was filtered off using a Celite pad and the solution was evaporated to dryness. The crude material was dried under vacuum, giving a yield of 4.5 g (91%). The spectral data showed that the resultant compound was pure enough to be utilized in the next synthesis step without additional purification.

$^1$H NMR (300 MHz, CDCl$_3$) δ 7.92-7.88 (1H, m), 7.85-7.82 (1H, m), 7.74-7.67 (2H, m), 0.26 (9H, s).

$^{13}$C NMR (75.4 MHz, CDCl$_3$) δ 175.57, 133.74, 133.09, 132.77, 130.41, 124.30, 103.12, 100.30, −0.71.

2-(3'-Trimethylsilylpropionyl)-aniline (3)

2-(3'-Trimethylsilylpropiolyl)-nitrobenzene (11) (500 mg) was dissolved in anhydrous toluene (8 mL). Palladium on carbon (30 mg) was added and the reaction mixture was placed under hydrogen atmosphere provided by a balloon. The reaction mixture was stirred at room temperature for 24 hours. After completion of the reaction, the palladium on carbon was filtered off using a Celite pad and the solution was concentrated under vacuum. The crude material was purified by silica gel column and provided a yield 380 mg (86%).

$^1$H NMR (300 MHz, CDCl$_3$) δ 7.93-7.90 (1H, m), 7.47-7.41 (1H, m), 6.86-6.81 (1H, m), 6.45 (2H, brs), 3.12-3.06 (2H, m), 1.11-1.05 (2H, m), 0.23 (9H, s).

$^{13}$C NMR (75.4 MHz, CDCl$_3$) δ 204.12, 150.58, 134.28, 131.26, 117.60, 115.93, 33.96, 11.82, −1.54.

BNP1350

A-Ring (3) (16.8 mg) and CDE-ring (4) (20 mg) were dissolved in a mixture of acetic acid and toluene (1 mL; 1:1 v/v). P-Toluensulfonic acid (1 mg) was added and the reaction mixture was stirred at 100° C. for 24 hours. The reaction mixture was cooled to room temperature and concentrated under reduced pressure. The residue was washed 2-times with hexane (2×10 mL) and dried under vacuum. The crude material was purified by silica gel column providing a yield of 32 mg (94%) of the BNP1350 (Karenitecin; Cositecan) product.

Scheme 4 illustrates the fourth process of the present invention employed to synthesize BNP1350. The starting reagent was commercially available cost effective ethynyltrimethylsilane to which solutions of n-butullithium and o-nitrobenzaldehyde were added to form 1-(2-Nitrophenyl)-3-trimethylsilyl-2-propyn-1-ol (10). Oxidation of propyn-1-ol (10) with manganese dioxide-generated 2-(3'-trimethylsilylpropiolyl)-nitrobenzene (11), which was concerted to the key A-ring moiety 1-(2-amino-phenyl)-3-trimethylsilanyl-propan-1-one (3) by hydrogenation in presence of Pd/C. The Friedlander condensation of 1-(2-amino-phenyl)-3-trimeth- The spectral data was shown to be identical to that obtained for commercially available BNP1350.

5. Synthesis Scheme Five

Scheme 5 illustrates the fifth process of the present invention employed to synthesize BNP1350. As shown, the starting reagent was commercially available cost effective 2-nitrobenzoic acid (12). The process includes first conversion of 2-nitrobenzoic acid (12) to more active 2-nitrobenzoyl chloride (13) and following the Friedel-Craft alkynylation of the crude acid chloride (13) with bis(trimethylsilyl)acetylene to generate 1-phenyl-3-trimethylsilyl-propynone (11). Hydrogenation of crude (11) in presence of Pd/C produced the key A-ring moiety 1-(2-Amino-phenyl)-3-trimethylsilanyl-propan-1-one (3), and crystallization of the crude 3 in presence of 1 N HCl gave 1-(2-amino-phenyl)-3-trimethylsilanyl-propan-1-one salt (14). The Friedlander condensation of 1-(2-amino-phenyl)-3-trimethylsilanyl-propan-1-one salt (14) with the commercial available CDE ring moiety (4) gave the desired BNP1350 (Karenitecin; Cositecan) product with excellent yield.

2-Nitrobenzoyl chloride (13)

To the suspension of 2-nitrobenzoic acid (200 g) and a catalytic amount of dimethylformamide (DMF; 5 mL) in DCM (2.5 L) was added oxalyl dichloride (304 g) dropwise at room temperature over a 30 minute interval. After the addition, the reaction was continued stirring for approximately 1 hour at room temperature and the suspension turned into a clear solution. The completion of the reaction was monitored by TLC (generally ~1 hour). The reaction mixture was then concentrated at 35° C. to dryness to give 225 g of the crude product (13) as light yellow oil or solid (mp: 17° C., lit), which was directly used for the next step without further purification.

1-(2-Nitrophenyl)-3-(trimethylsilyl)prop-2-yn-1-one (11)

A solution of 2-nitrobenzoyl chloride (13) (225 g; 1.2 moles) and 1,2-bis(trimethylsilyl)ethyne (205 g; 1.2 moles) in dichloromethane (3 L) was cooled to 0° C. Aluminum chloride (159.2 gram, 1.2 moles) was slowly added at 0° C. over 10 minutes while keeping the internal reaction temperature below 10° C. After the addition, the reaction mixture was stirred at 5-10° C. for 1 hour. With stirring, the black reaction mixture was poured into ice-water mixture (2 kg of ice and 1 kg of water). The resulting suspension was filtered and the filter cake was washed with dichloromethane (200 mL). The organic phase of the combined filtrate was separated. The aqueous phase was extracted 2-times with dichloromethane (2×2 L). The combined organic phase was washed with water (2 L), filtered through a Celite pad (200 g), dried over sodium sulfate (120 g), and concentrated at the temperature below 30° C. (bath temperature) to dryness to give 294 g (99% yield) of the desired product in 95% HPLC purity.

$^1$H-NMR (300 MHz, CDCl$_3$) δ 7.92-7.89 (dd, J=7.49, 1.29 Hz, 1H), 7.86-7.83 (dd, J=7.50, 1.56 Hz, 1H), 7.76-7.66 (m, 2H), 0.27 (s, 9H).

1-(2-Aminophenyl)-3-(trimethylsilyl)propan-1-one (3)

To the solution of 1-(2-nitrophenyl)-3-(trimethylsilyl) prop-2-yn-1-one (11) (294 g; 1.19 mole) in toluene (4.5 L) was added Pd/C (10% wt; 30 g) under N$_2$. The resulting suspension was degassed under vacuum and back-filled 3-times with H$_2$. The mixture was hydrogenated under 0.3 MPa of hydrogen at room temperature for 72 hours. The progress of the reaction was monitored by HPLC. When the HPLC analysis indicated the disappearance of compound (II), the catalyst was filtered off through a Celite pad. The filtrate was concentrated under vacuum to give the crude product as black liquid. HPLC analysis showed 90% purity. The crude product was dissolved in ethyl acetate (7.5 L) and treated with 4N hydrochloric acid (600 mL). After the phase separation, HPLC analysis showed the 92.8% purity. The organic phase was washed again with 4 N hydrochloric acid (600 mL). The organic phase was further washed with 4 N hydrochloric acid (500 mL) one additional time. The organic phase was dried over sodium sulfate (200 g), concentrated to give the crude product (3) (220 g; 84% yield).

HPLC purity: 92.2%;
LC-MS: m/z 222 (MH$^+$);
$^1$H-NMR (300 MHz, CDCl$_3$) δ 7.76-7.73 (d, J=7.49 Hz, 1H), 7.30-7.24 (t, J=7.61 Hz, 1H), 6.69-6.64 (t, J=6.96 Hz, 2H), 6.27 (brs, 2H), 2.94-2.89 (m, 2H), 0.94-0.88 (m, 2H), 0.07 (s, 9H).

1-(2-Aminophenyl)-3-(trimethylsilyl)propan-1-one hydrochloride (14)

To the solution of crude (3) (220 gram, 92.2% HPLC purity) in ethyl ether (450 milliliter), was added saturated hydrochloric acid/ethyl ether solution dropwise at room temperature over 30 minutes. The precipitated solid was filtered, the filter cake was washed with mixed solvent (ethyl ether: n-hexane 1:1 v/v; 400 mL), and dried under high vacuum for 2 hours at room temperature to give the desired product (14) (160 g; yield: 62.4%) as a light tan solid. HPLC purity: 98%; LC-MS: m/z 222 (MH$^+$);
$^1$H-NMR (300 MHz, CDCl$_3$) δ 8.9 (brs, 3H), 8.05-8.03 (d, J=7.56 Hz, 1H), 7.30-7.24 (d, J=7.56 Hz, 1H), 7.69-7.64 (t, J=7.47 Hz, 1H), 7.53-7.48 (t, J=7.47 Hz, 1H), 3.06-2.97 (m, 2H), 0.92-0.87 (m, 2H), 0.06 (s, 9H).

BNP1350

To a solution of 1-(2-aminophenyl)-3-(trimethylsilyl)propan-1-one HCl salt (14) (1165.5 mg) and (4) (700 mg) in acetic acid (29 mL) and toluene (29 mL), was added p-toluenesulfonic acid (58.5 mg) to give a light yellow solution. The resulting solution was stirred at 100° C. for 24 hours. After cooled to room temperature, the solution was concentrated to dryness. The residue was slurried in isopropanol (12 mL) and stirred at room temperature for 30 minutes. The solid product was collected by vacuum filtration. The wet cake was washed 3-times with isopropanol (3×1 mL) to produce an off-white solid, which was dried in vacuo to give 820 mg (58.8% yield) of the desired BNP1350 (Karenitecin; Cositecan) product in 99.2% purity. $^1$H-NMR analysis was consistent with the structure BNP1350.

Alternate Method for the Synthesis of 1-(2-Nitrophenyl)-3-(trimethylsilyl)prop-2-yn-1-one (11)

A second method of synthesis may also be employed to generate the key intermediate 1-(2-nitrophenyl)-3-(trimethylsilyl)prop-2-yn-1-one (11) which is utilized in the aforementioned Synthesis Scheme 5 for the total chemical synthesis of BNP1350. As shown, commercially available ethynyltrimethylsilane (15) was treated with n-butullithium and zinc (II) chloride to form ((trimethylsilyl)ethynyl)zinc (II) chloride (16), which was then added to 2-nitrobenzoyl chloride (13) to yield the desired intermediate product, 1-(2-nitrophenyl)-3-(trimethylsilyl)prop-2-yn-1-one (11).

(Trimethylsilyl)ethynyl)zinc(II) chloride (16)

To a solution of trimethylsilylacetylene (500 mg) in THF (10 mL) under a N$_2$ atmosphere was added n-butyllithium (2.5 M in hexane; 2.45 mL) drop-wise at −78° C. and continued stirring for one hour at −78° C. Then a solution of zinc (II) chloride (1.18 g) in dry THF was added dropwise and stirring was continued for another 1 hour below −60° C. The reaction mixture was directly used for next coupling reaction with intermediate (13).

1-(2-Nitrophenyl)-3-(trimethylsilyl)prop-2-yn-1-one (11)

The above solution of (trimethylsilyl)ethynyl)zinc(II) chloride (16) in THF was warmed to 0° C., and added to the mixture of 2-nitrobenzoyl chloride (0.94 g) and tetrakis(triphenylphosphine) palladium(0) (176 mg) in tetrahydrofuran at 0° C. under a N$_2$ atmosphere. The reaction mixture was maintained at 0° C. for 30 minutes. Aqueous ammonium chloride solution was added to quench the reaction. It was then extracted 3-times with EtOAc (3×100 mL), dried over sodium sulfate, filtered and concentrated under vacuum. The residue was purified by preparative TLC to give 300 mg of the desired product (11).
$^1$H-NMR (300 MHz, CDCl$_3$) δ 7.92-7.89 (dd, 1H, J=7.49 Hz, J=1.29 Hz), 7.86-7.83 (dd, 1H, J=7.50 Hz, J=1.56 Hz), 7.76-7.66 (m, 2H), 0.27 (s, 9H).

Cytotoxicity Testing

A comparison of the cytotoxic potency of BNP1350 synthesized from naturally-isolated camptothecin versus BNP1350 synthesized via Total Synthesis Scheme set forth herein was performed.

BNP1350

Materials and Methods

Wild type human ovarian cancer cells (A2780/WT) and doxorubicin resistant human ovarian cancer cells (A2780/DX5) were cultured in RPMI 1640 medium supplemented with 10% fetal bovine serum and 2 mM glutamine, and grown in a 37° C. incubator with 5% CO$_2$. BNP1350 synthesized from camptothecin natural product (purchased from APAC)

and BNP1350 synthesized via the Total Synthesis Scheme at BioNumerik Pharmaceuticals, Inc. were dissolved in DMSO for use in cytotoxicity experiments where inhibition of cell growth was measured using the SRB assay. Briefly, cells were seeded (450 cells/well in 100 µL volume) in a 96-well microtiter plates and allowed to attach for 24 hours prior to treatment with either natural product BNP1350 or total synthesis BNP1350 for 2 hours. Following this 2 hour treatment, BNP1350 was removed, the cells were washed with drug-free media (200 µL), and then drug-free media (200 µL) was added to the cells which were allowed to continue growing at 37° C. with 5% $CO_2$ before the SRB assay was performed (total experimental time from the time of initial seeding was 5 days, during which 5 cell doublings occurred).

Figure 2:
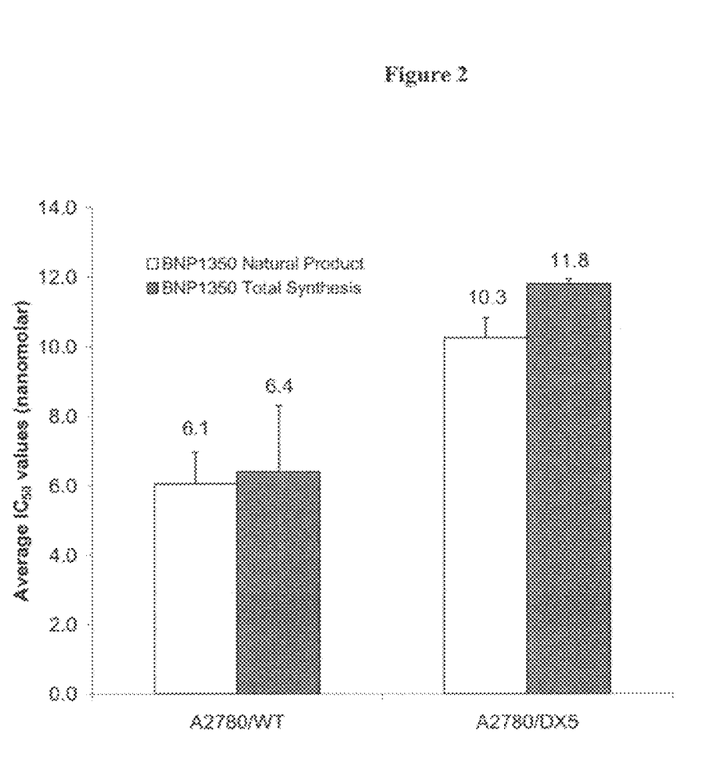
FIG. 2 illustrates a summary of average IC50 values for BNP1350 prepared from natural product and BNP1350 prepared via total synthesis scheme of the present invention.

Results $IC_{50}$ values for BNP1350 prepared from natural product or prepared via total synthesis were very similar (see, Table 1; Graph 2) and both BNP1350 preparations were shown to be potent inhibitors of A2780/WT and A2780/DX5 cell growth with nanomolar IC50 values. Both BNP1350 test articles also exhibited potency in both wild-type and doxorubicin resistant ovarian cancer cells (see, Table 1, Table 2, Graph 2) with resistance factor ratios that were less than 2.0 (see, Table 2).

TABLE 1

Summary of $IC_{50}$ Determinations in Human Ovarian Cancer Cells

|  | Test 1 | Test 2 | Average | STD |
|---|---|---|---|---|
| $IC_{50}$ (nM) A2780/WT | | | | |
| Natural Product BNP1350 | 6.7 | 5.4 | 6.1 | 0.9 |
| Total Synthesis BNP1350 | 6.0 | 6.8 | 6.4 | 0.8 |
| $IC_{50}$ (nM) A2780/DX5 | | | | |
| Natural Product BNP1350 | 8.9 | 11.6 | 10.3 | 1.9 |
| Total Synthesis BNP1350 | 11.9 | 11.7 | 11.8 | 0.1 |

TABLE 2

Summary of Resistance Factor Ratios

|  | Resistance Factor Ratio A2780/DX5 $IC_{50}$/A2780WT $IC_{50}$ |
|---|---|
| Natural Product BNP1350 | 1.7 |
| Total Synthesis BNP1350 | 1.8 |

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The present invention has been described broadly and generically herein. Each of the narrower species and subge- neric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and applicants reserve the right to revise the application or claims to refer specifically to any individual member or any subgroup of members of the Markush group.

Other embodiments are within the following claims. The patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

What is claimed is:

1. A method for the total chemical synthesis of 7-(2'-trimethylsilyl)ethyl camptothecin (Karenitecin), wherein said method is set forth in Synthesis Scheme 1 comprising the following steps:
   Step 1) The synthesis of the intermediate 1-(2-nitrophenyl)-3-trimethylsilanyl-propenone is performed by addition of 2-(trimethylsilyl)vinylmagnesium bromide to 2-nitrobenzaldehyde (1), followed by oxidation of the crude racemic benzylic alcohol intermediate to produce its corresponding vinyl trimethylsilyl aryl ketone. (2);
   Step 2) Hydrogenation of vinyl trimethylsilyl aryl ketone (2) in presence of Pd/C to produce the key A-ring synthone 1-(2-amino-phenyl)-3-trimethylsilanyl-propan-1-one (3); and
   Step 3) Organic acid catalyzed Friedlander condensation of 1-(2-amino-phenyl)-3-trimethylsilanyl-propan-1-one (3) with the commercially-available CDE ring chiral intermediate compound (4) to give enantiomerically pure 7-(2'-trimethylsilyl)ethyl camptothecin as the desired product 2. A method for the Total Chemical Synthesis of 7-(2'-trimethylsilyl)ethyl camptothecin (Karenitecin), wherein said method is set forth in Synthesis Scheme 2 comprising the following steps:
   Step 1) Treatment of N-Boc-aniline (5) with tert-butyl lithium, followed by addition to methoxymethyl(3-trimethylsilyl)propionamide (6) to generate 2-(3'-trimethylsilylpropionyl)-N-Boc-aniline (7); and
   Step 2) Organic acid catalyzed Friedlander condensation of 2-(3'-trimethylsilylpropionyl)-N-Boc-aniline (7) with the commercially-available chiral CDE ring intermediate compound (4) to give enantiomerically pure 7-(2'-trimethylsilyl)ethyl camptothecin as the desired product Step 1) Suzuki-type coupling of N-Boc-2-iodoaniline (8) with ethynyltrimethylsilane in presence of carbon monoxide to produce 2-(3'-trimethylsilylacetylenic ketone)-N-Boc-aniline intermediate (9), followed by hydrogenation in presence of Pd/C to generate 2-(3'-trimethylsilylpropionyl)-N-Boc-aniline (7); and Step 2) Organic acid catalyzed Friedlander condensation of 2-(3'-trimethylsilylpropionyl)-N-Boc-aniline (7) with the commercially-available chiral CDE ring intermediate compound (4) to give enantiomerically pure 7-(2'-trimethylsilyl)ethyl camptothecin as the desired product

3. A method for the Total Chemical Synthesis of 7-(2'-trimethylsilyl)ethyl camptothecin (Karenitecin), wherein said method is set forth in Synthesis Scheme 3 comprising the following steps:

4. A method for the Total Chemical Synthesis of 7-(2'-trimethylsilyl)ethyl camptothecin (Karenitecin), wherein said method is set forth in Synthesis Scheme 4 comprising the following steps:

Step 1) Synthesis of 1-(2-nitrophenyl)-3-trimethylsilyl-2-propyn-1-ol (10) by the addition of THF solution of n-butyllithiated trimethylsilane to o-nitrobenzaldehyde (1) at cryogenic conditions;

Step 2) Oxidation of propyn-1-ol (10) with manganese dioxide to generate 2-(3'-trimethylsilylpropiolyl)-nitrobenzene (11), and which was subsequently converted to the key A-ring synthone 1-(2-amino-phenyl)-3-trimethylsilanyl-propan-1-one (3) by hydrogenation in presence of Pd/C; and Step 3) Organic acid catalyzed Friedlander condensation of 1-(2-amino-phenyl)-3-trimethylsilanyl-propan-1-one (3) with the commercially-available chiral CDE ring intermediate compound (4) to give enantiomerically pure 7-(2'-trimethylsilyl)ethyl camptotbecin as the desired product

5. A method for the Total Chemical Synthesis of 7-(2'-trimethylsilyl)ethyl camptothecin (Karenitecin), wherein said method is set forth in Synthesis Scheme 5 comprising the following steps:

Step 1) Conversion of 2-nitrobenzoic acid (12) to the more reactive 2-nitrobenzoyl chloride (13);

Step 2) Friedel-Craft alkynylation of the crude 2-nitrobenzoyl chloride (13) with bis(trimethylsilyl)acetylene to generate 1-nitrophenyl-3-trimethylsilyl-propynone (11);

Step 3) Hydrogenation of the crude 1-nitrophenyl-3-trimethylsilyl-propynone (11) in the presence of Pd/C to produce the key A-ring synthone 1-(2-Amino-phenyl)-3-trimethylsilanyl-propan-1-one (3), followed by the crystallization of the crude 1-(2-Amino-phenyl)-3-trimethylsilanyl-propan-1-one (3) in presence of 1 N HCl to give the 1-(2-amino-phenyl)-3-trimethylsilanyl-propan-1-one hydrochloride salt (14); and Step 4) Organic acid catalyzed Friedlander condensation of the 1-(2-amino-phenyl)-3-trimethylsilanyl-propan-1-one hydrochloride salt (14) with the commercially-available chiral CDE ring intermediate compound (4) to give enantiomerically pure 7-(2'-trimethylsilyl)ethyl camptothecin as the desired product

* * * * *